United States Patent [19]

Lekhgolts et al.

[11] Patent Number: 5,569,211
[45] Date of Patent: Oct. 29, 1996

[54] SINGLE-USE HYPODERMIC SYRINGE

[76] Inventors: Victor Lekhgolts, 817 N. Croft Ave. #C, Los Angeles, Calif. 90069; Oleg Shvabsky, 1422 N. Martel Ave. #7, Los Angeles, Calif. 90046

[21] Appl. No.: 461,494

[22] Filed: Jun. 5, 1995

[51] Int. Cl.$^6$ ..................................................... A61M 5/32
[52] U.S. Cl. ........................ 604/195; 604/110; 128/919
[58] Field of Search ................................. 604/110, 194, 604/195, 196, 197, 198, 218, 222; 128/919

[56] References Cited

U.S. PATENT DOCUMENTS

| | | | |
|---|---|---|---|
| 5,125,908 | 6/1992 | Cohen | 604/196 |
| 5,380,286 | 1/1995 | van den Haak | 604/110 |
| 5,401,249 | 3/1995 | Shields | 604/110 |

*Primary Examiner*—Corrine M. McDermott
*Assistant Examiner*—Cris L. Rodriguez

[57] ABSTRACT

A single-use hypodermic syringe has barrel (10) and needle holder (20) with a needle receiving passage. The needle holder is detachably mounted in the barrel and defines annular space (30) with the barrel communicating with the needle receiving passage. Piston (32) is mounted in annular space (30) and piston rod (38) is connected to the piston with an amount of lost motion. Needle holder (20) is connectable to the piston rod by means of elastically mounted projection (26) engageable with projection (50) of the piston rod. The amount of the lost motion is greater than the total of the axial lengths of projections (26, 50) of piston rod (38) and needle holder (20).

4 Claims, 3 Drawing Sheets

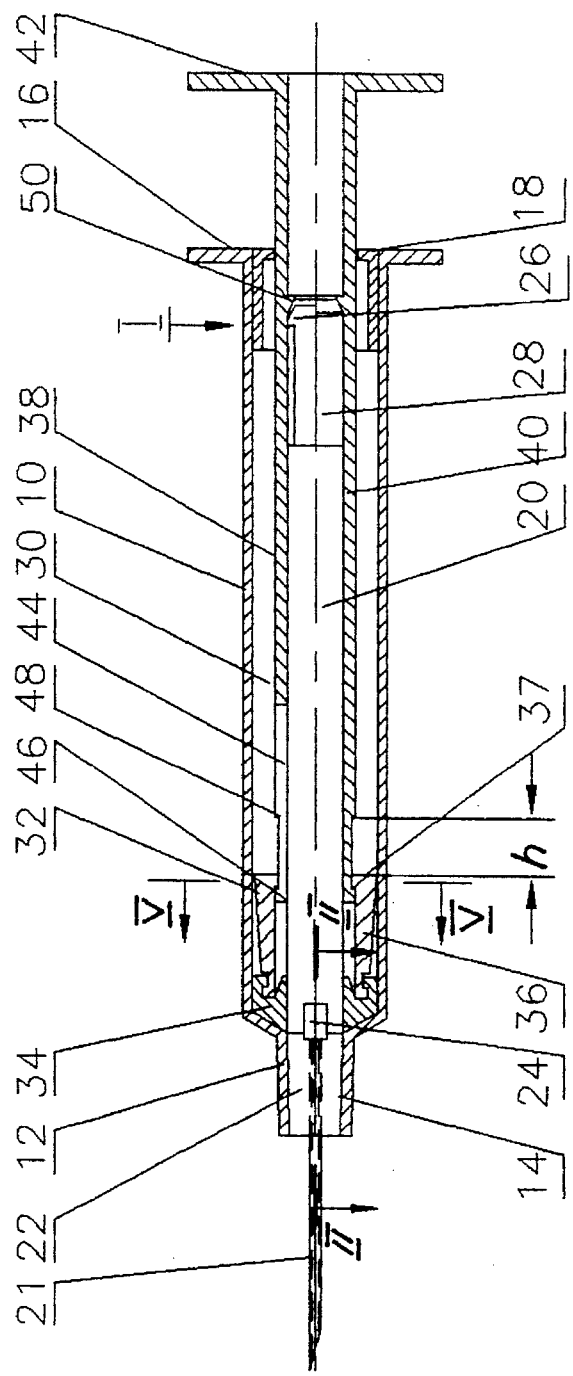
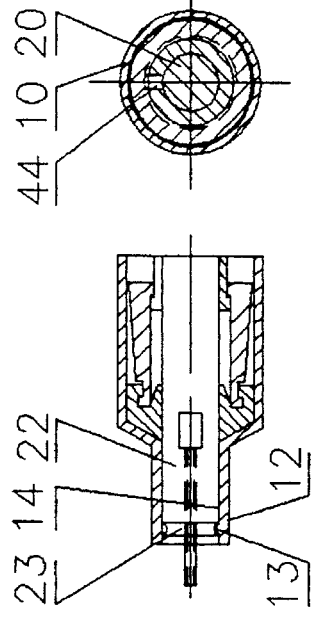
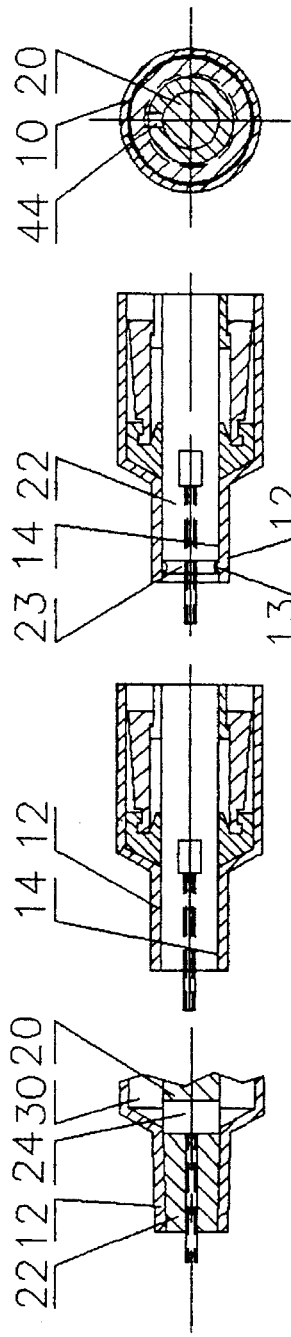
Fig. 1
Fig. 3
Fig. 4
Fig. 2
Fig. 5

SINGLE-USE HYPODERMIC SYRINGE

FIELD OF THE INVENTION

The invention relates to the medical field and deals with single-use hypodermic syringes using a so called safe syringe system. More particularly, the invention relates to syringe systems that become unfit for reuse upon an attempt to reuse. Still more specifically, the invention relates to safety syringe systems that are protected against reuse by a positive retraction of the needle into the barrel without the possibility of its extension from the barrel.

BACKGROUND OF THE INVENTION

Single-use hypodermic syringes can have different devices for inhibiting their reuse. Strictly speaking, these safety devices are divided into those intended to inhibit reuse by any user and those designed to hinder an accidental reuse by medical personnel. Syringes having positively retracted needles are mostly designed for use in clinics and other medical institutions as a simple means for hindering an accidental reuse.

A prior art syringe (U.S. pat. No. 5,215,533) has a device for vacuum retraction of the needle that consists of a vacuum seal of the piston and a vacuum seal of a needle holder installed in the syringe barrel. The combination of vacuum seals are intended to insure retraction of the needle after the establishment of a vacuum tight connection between the needle holder and piston. This prior art syringe is complicated and requires the use of special materials for insuring a reliable vacuum coupling. It should be noted that various factors can interfere with the reliable vacuum coupling between the needle holder and piston. In addition, the vacuum seals of the piston and needle take a certain space between the needle receiving part of the syringe barrel and the piston so that a part of an injection fluid will be left over.

SUMMARY OF THE INVENTION

It is an object of the invention to provide a single-use hypodermic syringe having a simple mechanical device for positively retracting the needle which is reliable and consists of a small number of parts.

It is also an object of the invention to provide a single-use hypodermic syringe with a positively retractable needle holder which is so constructed as to insure complete injection of an injection fluid.

Another object of the invention is to provide a single-use hypodermic syringe that is so constructed as to positively prevent medical personnel from touching the needle after injection.

Finally, it is an object of the invention to provide a single-use hypodermic syringe with a positively retractable needle that can be made of traditional materials and is easy to manufacture.

With these and other object in view, a single-use hypodermic syringe according to the invention has a barrel, a needle holder that has a needle receiving passage and is detachably mounted in the barrel to define an annular space with the barrel communicating with the needle receiving passage. A piston is mounted for reciprocation in the annular space and has a piston rod connected to the piston through a lost motion means. The syringe has a device for connecting the needle holder to the piston rod in the form an elastic shank of the needle holder having an elastically mounted projection engageable with a projection of the piston rod. The amount of the lost motion is greater than the total of the axial lengths of the projections of the piston and needle holder.

The barrel have a bore in its needle end and needle holder has an outer periphery. The periphery of the needle holder and the bore of the needle end of the barrel are tapered with an angle of taper that is smaller than the self braking angle of taper.

The above and other objects and advantages of the invention will become apparent from the following detailed description of its preferred embodiment illustrated in the accompanying drawings.

DESCRIPTION OF THE DRAWINGS

FIG. 1 is a longitudinal sectional view of a single-use hypodermic syringe according to the invention illustrating the syringe in its initial positions of delivery from factory;

FIG. 2 is a partial enlarged sectional view taken along line II—II in FIG. 1 (piston is not shown);

FIG. 3 shows an embodiment of the front end part of the syringe of FIG. 1;

FIG. 4 shows another embodiment of the front end part of the syringe of FIG. 1;

FIG. 5 is a sectional view taken along line V—V in FIG. 1;

DESCRIPTION OF EMBODIMENTS

Figure 6:
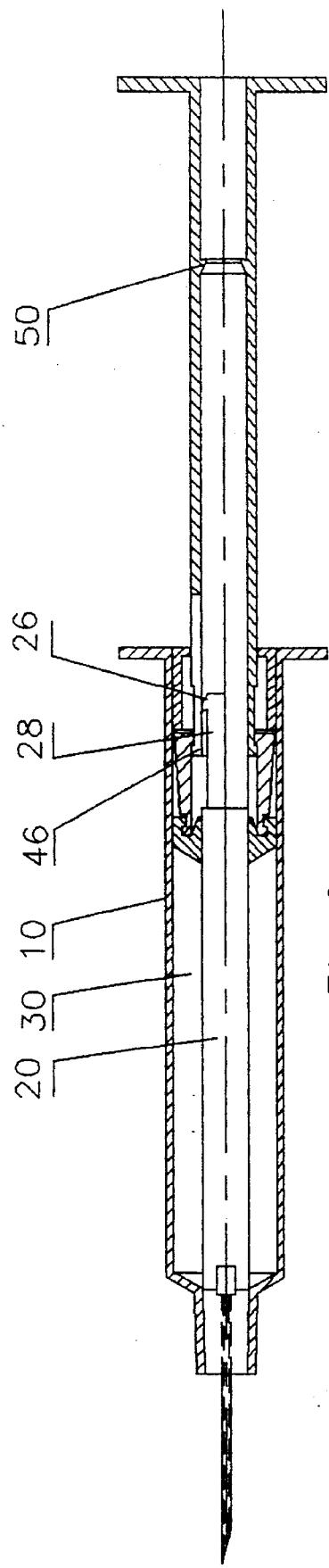
FIG. 6 shows the syringe of FIG. 1 after filling the syringe with an injection fluid.

With reference to FIG. 1, a single-use hypodermic syringe has a barrel 10 having a needle end 12 with a bore 14 and an opposite open end 16 with a flange for gripping by hand. Barrel has a guide bushing 18 for the purpose to be described later. A needle holder 20 is installed in bore 14 of barrel 10 and has a needle 21 secured in any appropriate known manner. The needle holder also has a needle end portion 22 with a needle receiving passage in which a needle 21 is installed in a known per se manner and a hole 24 communicating with the needle receiving passage. Hole 24 defines a diametrical passage in needle holder 20 (FIG. 2). The needle holder has an outward elastically mounted projection 26 protruding toward open end 16 of the barrel for the purpose to be described later. Projection 26 is made on an elastic shank 28 that is made of an elastic material, preferably integrally with needle holder 20, and that is yieldable.

It will be apparent from FIG. 1 that needle holder 20 has its needle end 22 seated in bore 14 of barrel 10. In the embodiment shown in FIG. 1, bore 14 of barrel 10 is tapered, with an angle of taper that is smaller than the locking angle. The periphery of needle end portion 22 of the needle holder is similarly tapered with an angle of taper that is smaller than the locking angle. The term "locking angle" means the angle at which friction between two parts becomes strong enough to hold ("lock", "stop", or "fix") the parts together. In other words, bore 14 of the barrel and end portion 22 of the needle holder have a mating taper preventing any inadvertent disengagement of the needle holder from the barrel during normal handling and use of the syringe. The normal handling and use of the syringe involves its filling and making an injection using standard injection techniques. Therefore, the tapered joint described above has to withstand a force applied to the needle in making an injection.

As shown in FIG. 3 the needle holder and barrel do not have the above-mentioned taper. In this embodiment there is a positive engagement between these two parts of the syringe that can be achieved by many appropriate known ways. These include a force fit (e.g., a shrink fit and the like), use of special not hardening adhesive compounds, and the like. It is understood that while the force fit can be of any amount, it is preferred to make choice of this force fit in such manner that the joint between the above-mentioned two parts of the syringe could withstand the force applied at injection without disconnection of the joint. As shown in FIG. 4, engagement between the barrel and needle holder is the same as that shown in FIG. 3. An internal annular sealing projection 13 is provided on the surface of needle end 12 of the barrel and an annular groove 23 is made in the needle end 22 of needle holder to receive projection 13. Projection 13 should have a certain degree of elasticity to insure separation of the barrel and needle holder. Similarly to the embodiments shown in FIGS. 1 and 3, the joint between barrel 10 and needle holder 20 has not to be detachable under a force applied to the needle during a normal injection procedure, and these two components must separate only if a certain force is applied to pull the needle holder. It is understood that in all embodiments shown in FIGS. 1 through 4 the joint between the needle holder and barrel at the front end of the barrel has to insure a reliable sealing and separation of the parts if a certain force is applied to the needle holder to pull it the direction toward open end 16 of barrel 10 as described below.

Needle holder 20 defines with barrel 10 an annular space 30, and the needle receiving passage (or the interior of needle 21) communicates with this annular space through hole 24. A piston 32 is installed in barrel 10, in annular space 30. The piston surrounds needle holder 20 and has a front sealing part 34 preferably made of an elastic sealing material, and a rear portion 36 having an internal projection 37 provided for the purpose to be described later. Piston 32 is moved in barrel 10 by means of a piston rod 38 that consists of a hollow cylindrical part 40 and a flange grip portion 42. Piston rod 38 has an elastic leg 44 with an outer projection 46 received in the rear part of piston 32 and engageable with internal projection 37 of the piston. The elastic leg has another outer projection at 48 spaced at a certain distance from projection 46. Piston rod 38 is mounted for axial movement in barrel 10 relative to barrel 10 and piston 32.

The amount of the axial movement of piston rod 38 with respect to piston 32 is defined by the spacing of projections 46 and 48 of elastic leg 44 of piston rod 38 and axial length of projection 37 of piston 32. This combination of projections 46 and 48 of elastic leg 44 and the internal projection 37 of the piston form a lost motion means connecting the piston rod to the piston with the amount of lost motion shown at "h" in FIG. 1.

It will be understood to those skilled in the art that other forms of the lost motion means can be used herein. Thus piston can have elastic projections for receiving the end of the piston rod, or any other appropriate forms of joint between the piston and piston rod could be used. They are well known to those skilled in the art and do not have any material bearing, on the invention. The purpose of the lost motion means here is to ensure a certain amount of free movement of the piston rod relative to the piston when the piston rod is pushed toward the needle end of barrel 10 with the piston approaching the position shown in FIG. 1 as described in greater detail below. In other words, this lost motion means provides for a certain delay between the movement of the piston rod and the movement of the piston. It will be apparent from FIG. 1 that piston rod 38 is guided in barrel 10 by means of guide bushing 18 at one end of the barrel and by means of piston 32 at the other end of the barrel. Piston rod 38 may have a guide collar (not shown), and in this case bushing 18 can be dispensed with. The position of needle holder 20 as shown is defined by its fitting in bore 14 of barrel 10 and by the inner surface of piston rod 38.

As shown in FIG. 1, piston rod 38 has an inward projection 50 that forms part a device for connecting the piston rod to the needle holder. The device for connecting the needle holder to the piston rod includes outer elastic projection 26 of elastic shank 28 of-needle holder 20 and internal projection 50 of piston rod 38. Both projections have tapered portions facing each other as shown in the drawing and inclined at a sharp angle in the direction toward the needle end of barrel 10. In the initial position shown in FIG. 1 (as delivered from factory) the relative position of projections 26 and 50 is as shown, with elastic projection 26 of needle holder 20 on the side of internal projection 50 facing toward the needle end of barrel 10. It is important that the amount of lost motion "h" be greater than the total axial length of projections 26 and 50. The purpose of this will be explained later.

OPERATION OF THE SYRINGE OF THE INVENTION

When the above-described hypodermic syringe is used, piston rod 38 is first pulled back to fill the syringe. When the piston rod is pulled, its projection 46 pulls piston. 32 which moves toward open end 16 of barrel 10 to reduce pressure in annular space 30. This pressure reduction is transmitted to the interior of needle 21 through hole 24, and an injection fluid is taken from a container (not shown) through needle 21 into annular space 30. The end position of the various parts of the syringe during its filling is shown in FIG. 6.

Figure 7:
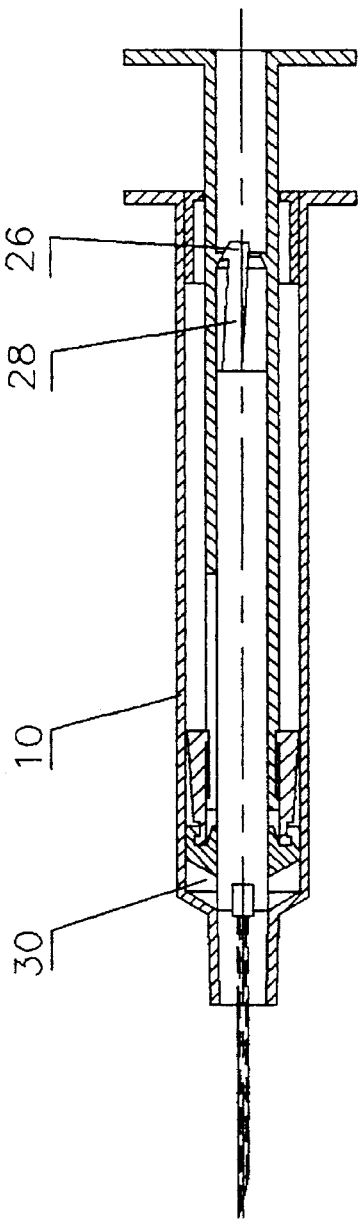
FIG. 7 shows a detail illustrating a relative position of parts of the syringe, during movement of the piston rod at the end of the injection stroke.

For making injection, piston rod 38 is pushed forward, in the direction toward needle end of barrel 10. At the beginning of this forward movement piston rod 38 will move with respect to piston 32 because of the lost motion connection between them. When projection 48 of elastic leg 44 of piston rod 38 will bear against rear part 36 of the piston, piston 32 will start-moving under the pushing action of the piston rod to displace the fluid from annular space 30 through hole 24 and through needle 21 to make injection. When piston 32 approaches the end of the injection stroke, internal projection 50 comes to bear against stationary elastic projection 26 of elastic shank 28 of needle holder 20. Further movement of piston rod 38 results in elastic shank 28 being slightly bent so as to allow internal projection 50 to pass over elastic projection 26 (FIG. 7).

Figure 8:
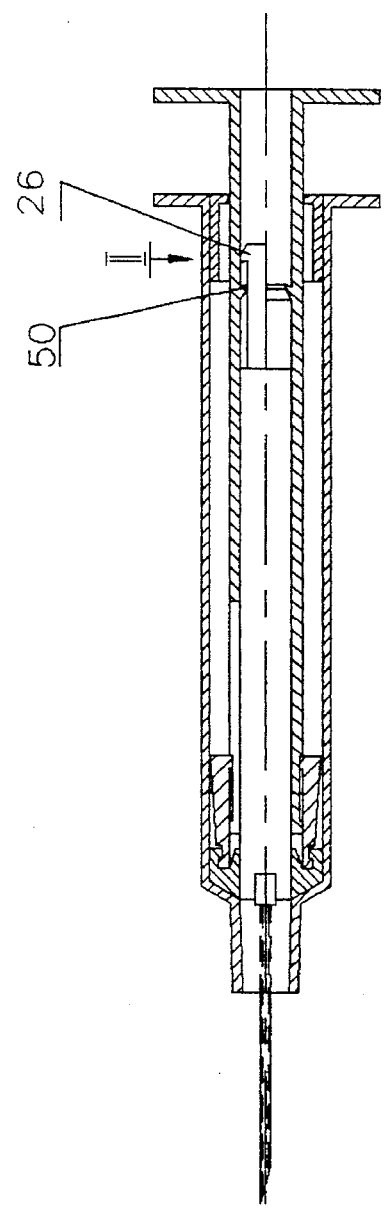
FIG. 8 shows the syringe in the position after the injection.
Figure 9:
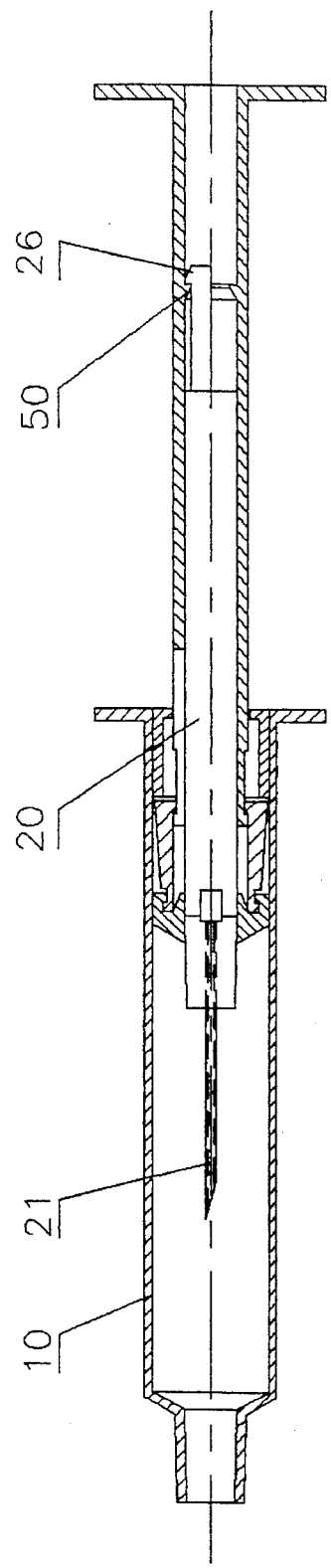
FIG. 9 shows various parts of the syringe after an attempt to refill the syringe.

At the end of the injection stroke (FIG. 8), piston 32 will bear against the needle end of barrel 10, and elastic projections 26 and 50 will be positioned as shown with a small space between them. If an attempt is now made to refill the syringe by pulling back piston rod 38, a projection 50 will engage projection 26, and needle holder 20 will be pulled back by the piston rod. This is possible because needle holder 20 is not rigidly secured in barrel 10. If any force stronger than that usually applied in the normal injection procedure is applied to the needle holder, needle holder 20 will move to a position shown in FIG. 9 at the end of the pulling stroke of piston rod 38. Now needle 21 is within barrel 10, and if the piston rod is pushed forward, it will push only piston 32. Thus the syringe cannot be used for a new injection because it cannot be refilled. In this position any contact of medical personnel with the needle is prevented as needle 21 is fully retracted into barrel 10 and cannot be extended outside.

It will be apparent from the above disclosure that the single-use syringe according to the invention reliably inhibits its reuse thanks to a positive mechanical retraction of the needle by means a simple purely mechanical device.

Various modifications and changes can be made in the above-described construction. Thus the needle holder can have a collet shank with a plurality of projections instead of the elastic shank, or piston rod can have an elastic projection engageable with a rigid projection of the needle holder.

We claim:

1. A single-use hypodermic syringe comprising a barrel having an open end and a needle end, a needle holder having an end that has a needle receiving passage and an end facing toward said open end of said barrel, and is detachably mounted in said needle end of said barrel, said needle holder defining an annular space with said barrel communicating with said needle receiving passage of said needle holder, a piston in said annular space mounted for reciprocation from one end of stroke position to another between said needle end and said open end of said barrel, a piston rod in said annular space mounted for reciprocation, a lost motion means for connecting said piston to said piston rod, whereby said piston moves with a delay determined by an amount of lost motion provided by said lost motion means after a movement during of said piston rod during at least a part of said reciprocation of said piston rod, and a means for connecting said needle holder to said piston rod, said means for connecting said needle holder to said piston rod comprising an outer elastic projection of said needle holder at the end thereof facing toward said open end of said barrel, said outer elastic projection having an axial length, and an internal projection of said piston rod having an axial length, said internal projection of said piston rod being engageable with said outer elastic projection of said needle holder, the amount of said lost motion being greater than the total of said axial lengths of said outer elastic projection of said piston rod and said internal projection of said needle holder.

2. The single-use hypodermic syringe of claim 1, wherein said barrel has a bore in its needle end and said needle holder has an outer periphery at said end thereof that has said needle receiving passage, said periphery of said needle holder and said bore of said needle end of said barrel being tapered with an angle of taper that is smaller than the locking angle.

3. The single-use hypodermic syringe of claim 1, wherein said barrel has a bore in its needle end and said needle holder has an outer periphery at said end thereof that has said needle receiving passage, said outer periphery of said needle holder being installed in said bore with a force fit.

4. The single-use hypodermic syringe of claim 1, wherein said barrel has a bore in its needle end and said needle holder has an outer periphery at said end thereof that has said needle receiving passage, said outer periphery of said needle holder being installed in said bore with a force, said outer periphery having a groove and said bore having a sealing projection received in said groove.

* * * * *